United States Patent [19]

Nakamori et al.

[11] 4,211,840
[45] Jul. 8, 1980

[54] METHOD FOR PRODUCING D-α-AMINO ACID

[75] Inventors: Shigeru Nakamori, Yokohama; Kenzo Yokozeki, Kawasaki; Koji Mitsugi, Yokohama; Chikahiko Eguchi; Hisao Iwagami, both of Kawasaki, all of Japan

[73] Assignee: Ajinomoto Company, Incorporated, Tokyo, Japan

[21] Appl. No.: 897,003

[22] Filed: Apr. 17, 1978

[30] Foreign Application Priority Data

Jun. 8, 1977 [JP] Japan ............................. 52/67411
Oct. 3, 1977 [JP] Japan ............................ 52/118928
Dec. 26, 1977 [JP] Japan ............................ 52/157108

[51] Int. Cl.$^2$ .................... C12P 13/24; C12P 13/04
[52] U.S. Cl. ................................. 435/107; 435/106; 435/108; 435/109; 435/110; 435/113; 435/114; 435/115; 435/116
[58] Field of Search ............... 195/2, 29; 435/106, 435/107, 108, 109, 110, 111, 112, 113, 114, 115, 116, 280, 822, 824, 829, 830, 874

[56] References Cited

U.S. PATENT DOCUMENTS

| 3,964,970 | 6/1976 | Denelli et al. | 195/2 |
| 4,094,741 | 6/1978 | Yamada et al. | 195/29 |
| 4,111,749 | 9/1978 | Degen et al. | 195/2 |

FOREIGN PATENT DOCUMENTS 2631048 1/1977 Fed. Rep. of Germany ............ 195/2

Primary Examiner—Robert J. Warden
Attorney, Agent, or Firm—Oblon, Fisher, Spivak, McClelland & Maier

[57] ABSTRACT

D-α-amino acids are produced by contacting a 5-substituted hydantoin with an effective amount of an enzyme capable of converting the 5-substituted hydantoin to the D-α-amino acid produced by a microorganism in an aqueous medium at a pH in the range of 4 to 9, the microorganism being capable of utilizing the D-isomer of the 5-substituted hydantoin as the sole nitrogen source, but substantially incapable of utilizing the L-isomer of the 5-substituted hydantoin as the nitrogen source and the substituent of the 5-position being such that upon reaction with the enzyme, an optically active D-α-amino acid isomer is produced; and recovering the D-α-amino acid which accumulates in the aqueous medium.

13 Claims, No Drawings

METHOD FOR PRODUCING D-α-AMINO ACID

BACKGROUND OF THE INVENTION

This invention relates to a method for producing D-α-amino acids, particularly by an enzymatic process.

D-α-amino acids as a class constitute many compounds and have potential utility as agricultural chemicals or medicinal agents or they can be used as starting materials for these chemicals or medicinal agents. For example D-p-hydroxy phenylglycine can be used as a starting material for the antibiotic, amoxycillin.

It is known that D-α-amino acids can be prepared by chemically hydrolyzing 5-substituted hydantoins to DL-α-amino acids, and then separating the D-α-amino acids from the racemic hydrolysis reaction product. This method, however, is rather complex in that it requires the separation of D-isomers and racemization of the L-isomer of the amino acids.

It is also known that 5-substituted hydantoins can be enzymatically converted to L-α-amino acids (Japanese Published Examined Patent Application No. 13850/1967). It is further known that the 5-substituted hydantoins can be enzymatically converted to N-carbamyl-D-α-amino acids (Japanese Published Unexamined Patent Application No. 10484/1977, and Proceedings of 1977 Annual Meeting of the Agricultural Chemical Society of Japan p 215 (1977)). In the latter method, however, additional process steps are required to convert the N-carbamyl-D-α-amino acids to D-α-amino acids.

Therefore, a need has continued to exist for a simpler and more economic method of obtaining D-α-amino acids.

SUMMARY OF THE INVENTION

Accordingly, one object of the present invention is to provide a method of selectively converting 5-substituted hydantoin starting materials directly to D-α-amino acids.

Briefly, these objects and other objects of the present invention as hereinafter will become more readily apparent can be attained by a method of producing a D-α-amino acid by contacting a 5-substituted hydantoin with an effective amount of an enzyme capable of converting the 5-substituted hydantoin to the D-α-amino acid, produced by a microorganism in an aqueous medium at a pH in the range from 4 to 9, said microorganism being capable of utilizing the D-isomer of said 5-substituted hydantoin as the sole nitrogen source, but substantially incapable of utilizing the L-isomer of said 5-substituted hydantoin as the nitrogen source, and the substituent of said 5-position being such that upon reaction with said enzyme, an optically active D-α-amino acid isomer is produced; and recovering the D-α-amino acid which accumulates in the aqueous medium.

DESCRIPTION OF THE PREFERRED EMBODIMENTS

It has been found that a wide distribution of bacterial microorganisms exist which produce an enzyme capable of converting 5-substituted-hydantoins to D-α-amino acids. These bacteria can especially be found in the genera Pseudomonas, Achromobacter, Alcaligenes, Moraxella, Paracoccus and Arthrobacter. The microorganisms can grow in an environment in which the D-isomer of the 5-substituted-hydantoin of this invention is used as the sole nitrogen source, but cannot grow significantly in environments which utilize the L-isomer of the 5-substituted hydantoin as the nitrogen source.

The bacteria are most readily obtained by the following method: A sample of microorganisms is inoculated on a screening medium which contains, per deciliter, 0.5 g glucose, 0.01 g yeast extract, 0.1 g $KH_2PO_4$, 0.3 g $K_2HPO_4$, 50 mg $MgSO_4.7H_2O$, 1 mg $FeSO_4.7H_2O$, 1 mg $MnSO_4.4H_2O$, and 1.0 g of one of the D- or L-5-substituted-hydantoins of this invention. The pH of the screening medium is preferably maintained at a low pH to prevent racemization of the D- or L-isomer of the 5-substituted hydantoin. The inoculated medium is incubated at 30° C. for 1 to 10 days.

Representative specimens of microorganisms which are capable of producing the necessary enzyme are as follows:

*Pseudomonas solanacearum* AJ 11149 (FERM-P4078, NRRL B-11,255)
*Pseudomonas caryophylli* AJ 11150 (FERM-P4079, NRRL B-11,256)
*Pseudomonas diminuta* AJ 11151 (FERM-P4080, NRRL B-11,257)
*Pseudomonas diminuta* AJ 11152 (FERM-P4081, NRRL B-11,258)
*Achromobacter liquefaciens* AJ 11198 (FERM-P4228, NRRL B-11,259)
*Alcaligenes aquamarinus* AJ 11199 (FERM-P4229, NRRL B-11,260)
*Moraxella nonliquefaciens* AJ 11221 (FERM-P4348, NRRL B-11,261)
*Paracoccus denitrificans* AJ 11222 (FERM-P4349, NRRL B-11,262)
*Arthrobacter fragilus* AJ 11223 (FERM-P4350, NRRL B-11,263)

The taxonomic characteristics of the microorganisms mentioned above are as follows: (The experimental methods employed conformed to the methods described in "M. J. Pelczav; Manual of Microgiological Methods", and identifications were made according to "Bergey's Manual of Determinative Bacteriology".)

AJ 11149

(A) Morphological characteristics
 (1) Cell form: rods, 0.3–0.5×1.2–2 μm
 (2) Pleomorphism: none
 (3) Motility, flagellation: motile, polar flagella
 (4) Spore: absent
 (5) Gram stain: negative
 (6) Acid fast: negative
(B) Culture characteristics
 (1) Nutrient-agar plate: Moderate growth, circular, convex to pulvinate, glistening, smooth, entire, amorphous, opaque, viscid, rosy buff.
 (2) Nutrient-agar slant: Abundant growth, raised, filiform, soluble pigment not formed.
 (3) Nutrient broth: Ring, moderate growth, uniformly turbidic, viscid sediment.
 (4) Gelatin stab: not liquefied
 (5) Litmus milk: unchanged
(C) Physiological characteristics:
 (1) Reduction of nitrate: positive
 (2) Denitrification: positive
 (3) Test of methyl red: negative
 (4) VP-test: negative
 (5) Production of indole: negative
 (6) Production of hydrogen sulfide: negative
 (7) Hydrolysis of starch: negative (8) Utilization citrate: Koser's citrate medium; negative, Christensen's citrate medium; positive (9) Assimilation of inorganic nitrogen: Nitrate; positive, Ammonium; positive

(10) Formation of pigment: not formed

(11) Reaction of urease: positive

(12) Reactive of oxidase: positive

(13) Reaction of catalase: positive

(14) Growth range: grow up to 38° C., do not grow at 39° C., grow at pH 6to pH 10

(15) Aerobiosis: aerobic

(16) O-F test: 0

(17) Formation of acid and gas from carbohydrates

|  | acid | gas |
|---|---|---|
| L-arabinose | + | − |
| D-xylose | + | − |
| D-glucose | + | − |
| D-mannose | + | − |
| D-fructose | − | − |
| D-galactose | + | − |
| Maltose | + | − |
| Sucrose | + | − |
| Lactose | − | − |
| trehalose | + | − |
| D-sorbitol | − | − |
| D-mannitol | − | − |
| inositol | − | − |
| glycerine | + | − |
| starch | − | − |
| raffinose | − | − |
| adonitol | − | − |
| salicin | − | − |
| dulcitol | − | − |
| rhamnose | − | − |

(18) Assimilation of carbon sources:

| glucose | + | ethanol | − |
|---|---|---|---|
| fructose | + | testosterone | − |
| L-arabinose | − | arginine | − |
| saccharose | + | betaine | − |
| malonic acid salts | − | | |

(19) Nutritional requirement: none

(20) Arginine dihydrase: none

(21) Accumulation of poly-$\beta$-hydroxy-butyric acid: accumulated

According to the taxonomic characteristics mentioned above, AJ 11149 is identified as *Pseudomonas solanacearum*.

AJ 11150

(A) Morphological characteristics (1) Cell form: rods, 0.3~0.5×1.5~3 μm (2) Pleomorphism: none (3) Motility, flagellation: motile, polar flagella (4) Spore: absent (5) Gram stain: negative (6) Acid fast: negative (B) Culture characteristics (1) Nutrient-agar plate: abundant growth, circular, convex to pulvinate, entire, smooth, glistening, opaque, amorphous, viscid, milky to buff.

(2) Nutrient-agar slant: abundant growth, raised, filiform to spreading, soluble pigment not formed.

(3) Nutrient broth: abundant growth, membranous, uniformly turbidic, viscid sediment (4) Gelatin stab: not liquefied (5) Litmus milk: unchanged (C) Physiological characteristics (1) Reduction of nitrate: positive (2) Denitrification: positive (3) Test of methylred: negative (4) VP-test negative (5) Production of indole: negative (6) Production of hydrogen sulfide: negative (7) Hydrolysis of starch: negative (8) Utilization of citrate: Koser's citrate medium, positive; Christensen's citrate medium, positive.

(9) Assimilation of inorganic nitrogen: nitrate, positive; ammonia, positive

(10) Formation of pigment: not formed

(11) Urease: positive

(12) Oxidase: positive

(13) Catalase: positive

(14) Growth range: grows up to 39.2° C., does not grow at 42° C., grows at from pH 6 to pH 10

(15) Aerobiosis: aerobic

(16) O-F test: 0

(17) Formation of acid and gas from carbohydrates:

|  | acid | gas |
|---|---|---|
| L-arabinose | + | − |
| D-xylose | + | − |
| D-glucose | + | − |
| D-mannose | + | − |
| D-fructose | − | − |
| D-galactose | − | − |
| maltose | − | − |
| sucrose | + | − |
| lactose | − | − |
| trehalose | − | − |
| D-sorbitol | − | − |
| D-mannitol | − | − |
| inositol | − | − |
| glycerine | − | − |
| starch | − | − |
| raffinose | − | − |
| adonitol | − | − |
| salicin | − | − |
| dulcitol | − | − |
| rhamnose | − | − |

(18) Assimilation of carbon sources:

| glucose | + | D (−) - tartarate | − |
|---|---|---|---|
| D-xylose | + | meso-tartarate | − |
| D-ribose | + | adonitol | − |
| L-rhamnose | + | 2,3-butyleneglycol | + |
| levulinate | − | m-benzoic acid | − |
| citraconate | − | tryptamine | − |
| mesaconate | − | α-amylamine | − |
| arginine | + | erythritol | + |
| betaine | + | | |

(19) Nutritional requirements: none

(20) Arginine dihydrase: none

(21) Accumulation of poly-$\beta$-hydroxy-butyric acid: accumulated

According to the taxonomic characteristics mentioned above, AJ 11150 is identified with *Pseudomonas caryophylli*.

AJ 11151

(A) Morphological characteristics (1) Cell form: rods, 0.3–0.4×1.2–2 μm (2) Pleomorphism: none (3) Motility, flagellation: motile, polar flagella (4) Spore: absent (5) Gram stain: negative (6) Acid fast: negative
(B) Growth on various media
(1) Nutrient-agar plate: moderate growth, circular, convex, entire, smooth, glistening, opaque, amorphous, butyrous, buff to salmon.
(2) Nutrient-agar slant: moderate growth, effused, filiform to spreading, soluble pigment not formed.
(3) Nutrient broth: moderate growth, uniformly turbidic.
(4) Gelatin stab: not liquefied
(5) Litmus milk: unchanged
(C) Physiological characteristics:
(1) Reduction of nitrates: positive
(2) Denitrification: negative
(3) Test of methyl red: negative
(4) VP-test: negative
(5) Production of indole: negative
(6) Production of hydrogen sulfide: negative
(7) Hydrolysis of starch: negative
(8) Utilization of citrate: Koser's citrate medium, positive; Christensen's citrate medium, positive
(9) Assimilation of inorganic nitrogen: nitrate, positive; ammonium, positive.
(10) Formation of pigment: not formed
(11) Urease: negative
(12) Oxidase: positive
(13) Catalase: positive
(14) Growth range: grows up to 36.5° C., does not grow at 39° C., grows at from pH 6 to pH 9.
(15) Aerobiosis: aerobic
(16) O-F test: acid not produced
(17) Formation of acid and gas from carbohydrates

|  | acid | gas |
| --- | --- | --- |
| L-arabinose | − | − |
| D-xylose | − | − |
| D-glucose | − | − |
| D-mannose | − | − |
| D-fructose | − | − |
| D-galactose | − | − |
| maltose | − | − |
| sucrose | − | − |
| lactose | − | − |
| trehalose | − | − |
| D-sorbitol | − | − |
| D-mannitol | − | − |
| inositol | − | − |
| glycerine | − | − |
| starch | − | − |
| raffinose | − | − |
| adonitol | − | − |
| salicin | − | − |
| dulcitol | − | − |
| rhamnose | − | − |

(18) Assimilation of carbon sources

| glucose | − | cellobiose | − |
| --- | --- | --- | --- |
| DL-β-hydroxybutyrate | + | | |
| L-histidine | + | | |

(19) Nutritional requirement: biotine, pantothenic acid, vitamin $B_{12}$ and cystine.
(20) Accumulation of poly-β-hydroxy-butyric acid: accumulated According to the taxonomic characteristics mentioned above, AJ 11151 can be identified as *Pseudomonas diminuta*.

AJ 11152
(A) Morphological characteristics
(1) Cell form: rods, 0.3–0.4×1.2–2 μm
(2) Pleomorphism: none
(3) Motility, flagellation: motile, polar flagella
(4) Spore: absent
(5) Gram stain negative
(6) Acid fast: negative
(B) Growth on various media
(1) Nutrient-agar plate: moderate growth, circular, convex, entire, smooth, amorphous, glistening, opaque, butyrous, buff to salmon.
(2) Nutrient-agar slant: moderate growth, effused, filiform soluble pigment not formed.
(3) Nutrient broth: moderate growth
(4) Gelatin stab: not liquefied
(5) Litmus milk: unchanged
(C) Physiological characteristics
(1) Reduction of nitrate: positive
(2) Denitrification: negative
(3) Test of methyl red: negative
(4) VP Test: negative
(5) Production of indole: negative
(6) Production of hydrogen sulfide: negative
(7) Hydrolysis of starch: negative
(8) Utilization of citrate:
Koser's citrate medium, negative; Christensen's citrate medium, negative.
(9) Assimilation of inorganic nitrogen: nitrate, positive; ammonium, positive.
(10) Formation of pigment: not formed
(11) Urease: positive
(12) Oxidase: positive
(13) Catalase: positive
(14) Growth range: grows up to 38° C., does not grow at 40° C., grows at from pH 6 to pH 9
(15) Aerobiosis: aerobic
(16) O-F test: Acid is not produced
(17) Formation of acid and gas from carbohydrates:

|  | acid | gas |
| --- | --- | --- |
| L-arabinose | − | − |
| D-xylose | − | − |
| D-glucose | − | − |
| D-mannose | − | − |
| D-fructose | − | − |
| D-galactose | − | − |
| maltose | − | − |
| sucrose | − | − |
| lactose | − | − |
| trehalose | − | − |
| D-sorbitol | − | − |
| D-mannitol | − | − |
| inositol | − | − |
| glycerine | − | − |
| starch | − | − |
| raffinose | − | − |
| adonitol | − | − |
| salicin | − | − |
| dulcitol | − | − |
| rhamnose | − | − |

(18) Assimilation of carbon sources

| glucose | − | cellobiose | − |
| --- | --- | --- | --- |
| DL-β-hydroxybutyrate | + | histidine | + |

(19) Nutritional requirement: biotine, pantothenic acid, vitamin $B_{12}$ and cystine.

(20) Accumulation of poly-$\beta$-hydroxy-butyric acid: accumulated

According to the taxonomic characteristics mentioned above, AJ 11152 can be identified as *Pseudomonas diminuta*.

AJ 11198

(A) Morphological characteristics
  (1) Cell form: rods, 1-2×3-5 μm
  (2) Pleomorphism: none
  (3) Motility, flagellation: motile, peritrichrous flagella
  (4) Spore: absent
  (5) Gram stain: negative
  (6) Acid fast: negative
(B) Growth on various media
  (1) Nutrient-agar plate: abundant growth, circular, convex to pulvinate, entire, smooth, glistening, opaque, amorphous, viscid, milky to buff.
  (2) Nutrient agar slant: abundant growth, effused, filiform, soluble pigment is not formed.
  (3) Nutrient broth: abundant growth, membranous, uniformly turbidic, viscid sediment.
  (4) Gelatin stab: liquefied
  (5) Litmus milk: unchanged
(C) Physiological characteristics
  (1) Reduction of nitrate: positive
  (2) Denitrification: negative
  (3) Test of methyl red: negative
  (4) VP Test negative
  (5) Production of indole: negative
  (6) Production of hydrogen sulfide: negative
  (7) Hydrolysis of starch: negative
  (8) Utilization of citrate: Koser's citrate medium, positive; Christensen's citrate medium, positive.
  (9) Assimilation of inorganic nitrogen: nitrate, negative; ammonia, negative.
  (10) Formation of pigment: not formed
  (11) Urease: negative
  (12) Oxidase: positive
  (13) Catalase: positive
  (14) Growth range: grows at 15° to 35° C., optimum 20° to 25° C., grows at pH 6 to pH 9.

According to the taxonomic characteristics mentioned above, AJ 11198 can be identified as *Achromobacter liquefaciens*.

AJ 11199

(A) Morphological characteristics
  (1) Cell form: rods, 0.7×2-4 μm
  (2) Pleomorphism: none
  (3) Motility, flagellation: motile, peritrichrous flagella
  (4) Spore: absent
  (5) Gram stain: negative
  (6) Acid fast: negative
(B) Culture characteristics
  (1) Nutrient-agar plate: moderate growth, circular, convex to pulvinate, smooth, entire, glistening, opaque, butyrous, amorphous, rosy buff to honey.
  (2) Nutrient-agar slant: abundant growth, effused, filiform, soluble pigment not formed.
  (3) Nutrient broth: moderate growth, membranous, uniformly turbidic, ring, viscid sediment.
(C) Physiological characteristics:
  (1) Reduction of nitrates: negative
  (2) Denitrification: negative
  (3) Test of methyl red: negative
  (4) VP test: negative
  (5) Production of indole: negative
  (6) Production of hydrogen sulfide: positive
  (7) Hydrolysis of starch: positive
  (8) Utilization of citrate: Koser's citrate medium, positive; Christensen's citrate medium, positive.
  (9) Assimilation of inorganic nitrogen: nitrate, negative; ammonium, negative.
  (10) Formation of pigment: not formed
  (11) Urease: positive
  (12) Oxidase: positive
  (13) Catalase: positive
  (14) Growth range: grows at from 15° to 40° C., optimum: 20° to 25° C., grows at from pH 6 to pH 10.
  (15) Aerobiosis: aerobic
  (16) O-F test: both O and F negative
  (17) Formation of acid and gas from carbohydrates

|  | acid | gas |
|---|---|---|
| L-arabinose | ± | — |
| D-xylose | ± | — |
| D-glucose | + | — |
| D-mannose | ± | — |
| D-fructose | ± | — |
| D-galactose | ± | — |
| maltose | — | — |
| sucrose | — | — |
| lactose | — | — |
| trehalose | — | — |
| D-sorbitol | ± (weak) | — |
| D-mannitol | ± (weak) | — |
| inositol | ± (weak) | — |
| glycerine | ± (weak) | — |

(18) GC content in DNA 58.0%

According to the taxonomic characteristics mentioned above, AJ 11199 can be identified as *Alcaligenes aquamarinus*.

AJ 11221

(A) Morphological characteristics
  (1) Cell form: plump to short rods, 0.4-1×1-2.5 μm
  (2) Pleomorphism: none
  (3) Motility: none
  (4) Spore: absent
  (5) Gram stain: negative
  (6) Acid fast: negative
(B) Culture characteristics
  (1) Nutrient-agar plate: moderate growth, circular, convex to raised, entire, opaque, glistening, amorphous, smooth, white gray
  (2) Nutrient-agar slant: moderate growth, effused, filiform
  (3) Nutrient broth: uniformly turbid
  (4) Gelatin stab: not liquefied
  (5) Litmus-milk: not liquefied, slightly alkalified
(C) Physiological characteristics
  (1) Reduction of nitrates: positive
  (2) Denitrification: negative
  (3) MR-test: negative
  (4) VP-test: negative
  (5) Production of indole: negative
  (6) Production of hydrogen sulfide: negative
  (7) Hydrolysis of starch: negative
  (8) Utilization of citrate: Koser's citrate medium, negative; Christensen's citrate medium, positive.
  (9) Assimilation of inorganic nitrogen: nitrate, positive; ammonium, positive.
  (10) Formation of pigment: not formed

(11) Urease: negative
(12) Oxidase: positive
(13) Catalase: positive
(14) Growth range: grows up to 37° C., grows at from pH 6 to pH 9.
(15) Aerobiosis: aerobic
(16) O-F test: O
(17) Formation of acid and gas from carbohydrates:

|             | acid       | gas |
|-------------|------------|-----|
| L-arabinose | + (weak)   | —   |
| D-xylose    | + (weak)   | —   |
| D-glucose   | + (weak)   | —   |
| D-mannose   | —          | —   |
| D-fructose  | + (weak)   | —   |
| D-galactose | —          | —   |
| maltose     | —          | —   |
| sucrose     | —          | —   |
| lactose     | —          | —   |
| starch      | —          | —   |
| trehalose   | —          | —   |
| D-sorbitol  | —          | —   |
| D-mannitol  | —          | —   |
| inositol    | —          | —   |
| glycerol    | —          | —   |

(18) Oxidation of gluconic acid (Haynes' method): negative

(19) Utilization of malonic acid (Ewing et al's method): negative

(20) Deaminase of phenylalanine (Ewing et al's method): negative

(21) Decarboxylase (Møller's method):

| lysine   | — | ornithine | — |
|----------|---|-----------|---|
| arginine | — |           |   |

(22) Arginine dihydrase (Stanier et al's method): negative
(23) Hydrolysis of casein: negative
(24) Hydrolysis of DNA: negative
(25) Accumulation of poly-β-hydroxybutyrate: negative According to the taxonomic characteristics mentioned above, AJ 11221 can be identified as *Moraxella nonliquefaciens*.

AJ 11222

(A) Morphological characteristics
(1) Cell form: plump to short rods, 0.4–1×1–2.5 μm
(2) Pleomorphism: none
(3) Motility, flagellation: none
(4) Spore: absent
(5) Gram stain: negative
(6) Acid fast: negative (B) Culture characteristics
(1) Nutrient-agar plate: moderate growth, circular, convex to raised, smooth, entire, glistening, opaque, butyrous, amorphous, buff to milky.
(2) Nutrient-agar slant: moderate growth, effused, filiform.
(3) Nutrient broth: uniformly turbidic
(4) Gelatin stab: not liquefied
(5) Litmus milk: not liquefied, slightly alkalified (C) Physiological characteristics
(1) Reduction of nitrates: positive
(2) Denitrification: negative
(3) MR-test: negative
(4) VP-test: negative
(5) Production of indole: negative
(6) Production of hydrogen sulfide: negative
(7) Hydrolysis of starch: negative
(8) Utilization of citrate: Koser's citrate medium, negative; Christensen's citrate medium, positive.
(9) Assimilation of inorganic nitrogen: nitrate, positive; ammonium, positive.
(10) Formation of pigment: not formed
(11) Urease: negative
(12) Oxidase: positive
(13) Catalase: positive
(14) Growth range: grows up to 36° C., grows at from pH 6 to pH 10.
(15) Aerobiosis: aerobic
(16) O-F test: O
(17) Formation of acid and gas from carbohydrates

|             | acid       | gas |
|-------------|------------|-----|
| L-arabinose | +(weak)    | —   |
| D-xylose    | + (weak)   | —   |
| D-glucose   | + (weak)   | —   |
| D-mannose   | —          | —   |
| D-fructose  | + (weak)   | —   |
| D-galactose | —          | —   |
| maltose     | —          | —   |
| sucrose     | —          | —   |
| lactose     | —          | —   |
| trehalose   | —          | —   |
| D-sorbitol  | —          | —   |
| D-mannitol  | —          | —   |
| inositol    | —          | —   |
| glycerine   | —          | —   |
| starch      | —          | —   |

(18) Oxidation of gluconic acid (Haynes' method): negative

(19) Utilization of malonic acid (Ewing et al's method): negative

(20) Deamination of phenylalanine (Ewing et al's method): negative

(21) Decarboxylase (Møller's method):

| lysine    | — | arginine | — |
|-----------|---|----------|---|
| ornithine | — |          |   |

(22) Arginine dihydrase (Stainer et al's method): negative
(23) Decomposition of casein: negative
(24) Decomposition of DNA: negative
(25) Accumulation of poly-β-hydroxybutyrate: accumulated (D) GC-content in DNA: 65.4%

According to the taxonomic characteristics mentioned above, AJ 11222 can be identified as *Paracoccus denitrificans*.

AJ 11223

(A) Morphological characteristics
(1) Cell form: rods, 0.5–0.9×1.2–5.0 μm
(2) Pleomorphism: none
(3) Motility, flagellation: motile, peritrichrous flagella
(4) Spore: absent
(5) Gram stain: weakly positive
(6) Acid fast: negative (B) Culture characteristics (1) Nutrient-agar plate: moderate growth, circular, convex to unbonate, entire to undulate, amorphous, dull, rough, buff to straw.

(2) Nutrient-agar slant: moderate growth, effused to raised, filiform to spreading.

(3) Nutrient broth: ring, not turbidic (4) Gelatin stab: not liquefied (5) Litmus-milk: not liquefied, slightly alkalified (C) Physiological characteristics (1) Reduction of nitrates: positive (2) Denitrification: negative (3) MR-test: negative (4) VP-test: negative (5) Production of indole: negative (6) Production of hydrogen sulfide: negative (7) Hydrolysis of starch: negative (8) Utilization of citrate: Koser's citrate medium, negative; Christensen's citrate medium, negative.

(9) Assimilation of inorganic nitrogen: nitrate, positive; ammonium, positive.

(10) Formation of pigment: not formed

(11) Urease: negative

(12) Oxidase: positive

(13) Catalase: positive

(14) Growth range: grows up to 37° C., grows at from pH 6 to pH 9.

(15) Aerobiosis: aerobic

(16) O-F test: O

(17) Formation of acid and gas from carbohydrates

|  | acid | gas |
|---|---|---|
| L-arabinose | +(weak) | − |
| D-xylose | +(weak) | − |
| D-glucose | + | − |
| D-mannose | +(weak) | − |
| D-fructose | − | − |
| D-galactose | +(weak) | − |
| maltose | − | − |
| sucrose | +(weak) | − |
| lactose | − | − |
| trehalose | − | − |
| D-sorbitol | − | − |
| D-mannitol | +(weak) | − |
| inositol | +(weak) | − |
| glycerine | +(weak) | − |
| starch | − | − |

(18) Oxidation of gluconic acid (Haynes' method): negative.

(19) Utilization of malonic acid (Ewing et al's method): negative.

(20) Deamination of phenylalanine (Ewing et al's method): negative.

(21) Decarboxylase (Møller's method):

| lysine | − | ornithine | − |
|---|---|---|---|
| arginine | − | | |

(22) Arginine dihydrase (Stainer et al's method): negative

(23) Decomposition of casein: negative

(24) Decomposition of DNA: negative

(25) Accumulation of poly-β-hydroxybutyric acid: not accumulated

(26) Nutritional requirement: requiring biotine

(27) Assimilation of carbohydrates (Stainer's method):

| D-glucose | + | saccarate | − |
|---|---|---|---|
| trehalose | + | propionate | − |
| 2-keto-gluconate | − | butyrate | − |
| m-inositol | + | adonitol | − |
| L-valine | − | propylene-glycol | − |
| β-alanine | + | ethanol | − |
| DL-arginine | + | D-xylose | + |
| betaine | + | D-ribose | − |
| L-arabinose | + | L-rhamnose | + |
| saccrose | + | "polysorbate 80" | − |
| levulinate | − | malonate | − |
| citraconate | − | testosterone | − |
| meso-tartarate | − | cellobiose | − |
| D(-) - tartarate | − | DL-β-hydroxybutyrate | + |
| sorbitol | + | L-histidine | − |
| mesaconate | − | pantothenic acid | − |
| erythritol | − | acetate | + |
| 2,3-butyleneglycol | − | succinate | − |
| m-benzoic acid | − | citrate | − |
| p-benzoic acid | − | L-ornithine | + |
| tryptamine | − | 5-keto-gluconate | + |
| α-amyl amine | − | L-lysine | + |
| DL-lactic acid | + | L-alanine | − |
| D-fructose | + | dulcitol | − |

(28) GC-content in DNA: 60.6%

(29) Di-basic amino acid in cell-wall: lysine

According to the microbiological characteristics mentioned above, AJ 11223 belongs to the genus Arthrobacter. AJ 11223 cannot be identified with a known species of the genus Arthrobacter from the point of view of the amino acid pattern in the cell-wall, the gelatin decomposition, the motility, the vitamin-requirement, and the starch-decomposition. Thus, AJ 11223 can be considered as a novel species of Arthrobacter, and designated as *Arthrobacter fragilus*.

As far as the 5-substituted hydantoin starting material is concerned, very many hydantoins can be converted to D-α-amino acids by the method of this invention, and therefore, a very wide variety of 5-substituted hydantoins may be used in this invention. The 5-substituent, of course, should be chosen such that upon reaction with the enzyme, an optically active D-α-amino acid isomer is produced. Suitable 5-substituent groups for 5-substituted hydantoins include:

1. Straight, branched or cyclic saturated aliphatic hydrocarbon residues.

Examples: methyl, ethyl, propyl, iso-propyl, iso-butyl, 1-methyl-propyl, tert-butyl, cyclo-hexyl, and cyclo-pentyl residues.

2. Straight, branched, or cyclic unsaturated aliphatic hydrocarbon residues.

Examples: 2-propenyl, 2-propyl, 1-cyclohexenyl, and 1,4-cyclohexadienyl residues.

3. Straight, branched or cyclic saturated or unsaturated aliphatic hydrocarbons residues of which one or more hydrogen atoms are substituted with one or more second substituents.

Examples of the second substituents include: hydroxyl, carboxyl, sulfhydryl, alkylmercapto, amino, alkylamino, alkoxy, carbamoyl, guanidino, ureido, sulfoxyl, nitro, halogeno, acyl, amino-sulfenyl, arylmercapto, 4-imidazoyl, and 4-thienyl residues.

4. Aromatic hydrocarbon residues.

Examples: phenyl and naphthyl residues.

5. Aromatic hydrocarbon residues of which one or more hydrogen atoms are substituted with one or more second substituents.

Examples of the second substituents include: alkyl, alkenyl, cyclic alkyl or alkenyl, hydroxyl, alkoxyl, halogeno, benzyloxy, benzyloxymethyloxy, methoxy-methyloxy, acyloxy, acyl, aryloxy, aminosulfenyl, trifluoro-methyl, alkylmercapto, amino, acylamino, alkylamino, nitro, carboxyl, and carbamoyl residues.

6. Heterocyclic residues.

Examples: 2-thienyl, 5-thiazole, 4-imidazole, 2-furyl residues

7. Heterocyclic residues of which one or more hydrogen atoms are substituted with one or more second substituents. Suitable second substituents include those listed under "5." above.

When the microorganisms as mentioned above are cultured in conventional culture media, an enzyme capable of converting the hydantoin compounds to D-α-amino acids is produced mainly in the cells of the microorganisms and is present to a slight extent in the supernatant of the cultured liquid.

The culture media used can contain carbon sources, nitrogen sources, inorganic ions, and when required, minor organic nutrients. When the culture media contain small amounts of the 5-substituted hydantoins, the enzyme activity produced is generally much higher.

Suitable carbon sources include, for example, carbohydrates such as glucose, and sucrose; organic acids such as acetic acid; alcohols such as ethylalcohol, and hydrocarbons. Suitable nitrogen sources include, for example, ammonia and urea. Suitable inorganic ions include, for example, phosphates and magnesium, ferrous, calcium, and potassium salts. Suitable organic nutrients include, for example, vitamins, amino acids and crude materials containing such organic nutrients as yeast extract, peptone, bouillon, or corn steep liquor. Cultivation is carried out at a pH of from 4 to 8 and preferably at a temperature in the range from 25° to 40° C. under aerobic conditions. After a one-half to 2 days of cultivation, the enzyme is chiefly produced in the cells. Accordingly, a culture broth containing cells and intact cells can be used as the enzyme source. Moreover, a homogenate of cells, cells treated with supersonic waves, freeze-dried cells, or cells dried with organic solvents such as acetone are also preferably used as the enzyme source. The protein fraction separated, for example, from the homogenate of cells or from the sonicate of cells, by a conventional method such as gel-filtration or the salting-out method can be also used as the enzyme source. Cells or other enzyme sources as above can be used after immobilization. It is expected that there are more than one enzyme participating in the conversion of the 5-substituted hydantoins to the D-α-amino acids.

The conversion of the 5-substituted-hydantoins to D-α-amino acids can be carried out by contacting the 5-substituted hydantoins with the cells of the microorganisms of this invention in the culture media during the course of the cultivation of the microorganisms, or by contacting 5-substituted hydantoin with the cells or the enzyme sources as mentioned above in reaction media. When the 5-substituted hydantoin is contacted with the cells in culture media, the hydantoin is preferably added after the microorganism has partly or wholly propagated. In order to avoid inhibition of the growth of the microorganism by high concentrations of the hydantoin, the concentration of the hydantoin in the culture media should preferably be maintained at a low level by intermittently feeding small portions of the hydantoin to the culture media. The cultivation is continued until no further hydantoin is effectively converted to D-α-amino acids.

The reaction media in which the 5-substituted hydantoin is contacted with the cells or the enzyme sources may optionally contain anti-oxidants, surface active agents, coenzymes and/or hydroxylamine to improve the yield of D-α-amino acid. The reaction media are maintained preferably at a temperature from 10° to 70° C., and at a pH of 4 to 9 for 5 to 100 hours.

The D-α-amino acid which accumulates in the culture media or the reaction media can be recovered very easily in a conventional manner such as by using ion exchange resins, or precipitation of the amino acid product at its iso-electric point, since very little L-isomer of the α-amino acid product is produced.

Having generally described this invention, a further understanding can be obtained by reference to certain specific examples which are provided herein for purposes of illustration only, and are not intended to be limiting unless otherwise specified.

Quantitative analysis of D-α-amino acid in the following examples was carried out as follows: The amino acid was developed on filter paper (solvent; n-butanol 2 parts, acetic acid 1 part and water 1 part), and the paper was sprayed with a ninhydrin solution. The color-development was measured at 570 m$\mu$, after extraction with 50% ethanol. Quantitative analyses were conducted by liquid-chromatography. The D- and L-isomer contents were determined by measuring the optical rotation of the product.

EXAMPLE 1

An aqueous culture medium at pH 7.0 was prepared which contained, per deciliter, 0.5 g glucose, 0.5 g $(NH_4)_2SO_4$, 0.1 g $KH_2PO_4$, 0.1 g $K_2HPO_4$, 0.05 g $MgSO_4.7H_2O$, 1 mg $FeSO_4.7H_2O$, 1 mg $MnSO_4.4H_2O$, 1.0 g yeast extracts and 0.2 g DL-5-methylmercaptoethyl hydantoin. Fifty ml batches of the aqueous culture medium were placed in 500 ml flasks which were shaken and heated to sterilize at 120° C. for 15 minutes. *Pseudomonas caryophylli* AJ 11150, which was previously cultured on bouillon-agar slants at 30° C. for 24 hours, as a one-loopful inoculum was transferred from the bouillon-agar slants into each batch of the aqueous culture medium. Cultivation was carried out at 30° C. with shaking for 20 hours. The cells produced in the culture liquid were collected by centrifugation and washed with the same volume of physiological saline as the culture liquid. The cells thus obtained (5 g/dl) were suspended in samples of 0.1 M phosphate-buffer (pH 8.0) each containing 1 g/dl of the 5-substituted-hydantoins shown in Table 1 (final volume being 5 ml). Each reaction mixture was held at 30° C. for 16 hours.

The amounts of the D-α-amino acids produced in the reaction mixtures and the optical rotation of the amino acids were determined by the method mentioned before. Prior to the determination, cysteine and homocysteine in the culture liquid were oxidized to cystine and homocystine. The results are shown in Table 1.

Table 1

| 5-substituted-hydantoin used | D-α-amino acid formed | | Optical rotation of $[\alpha]_D^{20}$ | | |
|---|---|---|---|---|---|
| | | | the amino acid formed | authentic sample | measurement-conditions |
| DL-5-methyl hydantoin | D-alanine | 2.16 mg/ml | −14.3° | −14.7° | C = 1 | 6N-HCl |
| DL-5-isopropyl hydantoin | D-valine | 0.70 | −27.8° | −27.9° | C = 0.8 | " |
| DL-5-isobutyl hydantoin | D-leucine | 0.56 | −15.2° | −15.2° | C = 0.4 | " |
| DL-5-(1' methylpropyl)hydantoin | D-isoleucine | 1.21 | −38.2° | −40.7° | " | " |
| DL-5-hydroxymethyl hydantoin | D-serine | 3.91 | −14.1° | −14.6° | C = 1 | 2N-HCl |
| DL-5-(1'-hydroxyethyl) hydantoin | D-threonine | 2.82 | −27.4° | −28.5° | C = 0.6 | H₂O |
| DL-5-sulfhydrylmethyl hydantoin | D-cysteine + Dcystine | 4.84 | +220.7° | +222.5° | C = 0.2 | 1N-HCl |
| DL-5-methylmercaptoethyl hydantoin | D-methionine | 5.38 | −23.8° | −24.1°0.8 | | |
| DL-5-carbomoylmthyl hydantoin | D-asparagine | 4.82 | −30.8° | −31.3° | C = 0.2 | 3N-HCl |
| DL-5-carbamoylethyl hydantoin | D-glutamine | 4.26 | −6.7° | −6.6° | C = 0.4 | H₂O |
| DL-5-benzyl hydantoin | D-phenylalanine | 2.86 | +32.1° | +34.3° | C = 0.2 | " |
| DL-5-(p-hydroxybenzyl) hydantoin | D-tyrosine | 2.02 | +11.6° | +11.8° | C = 0.5 | 1N-HCl |
| DL-5-indolylmethyl hydantoin | D-tryptophan | 1.86 | +30.9° | +32.5° | C = 0.1 | H₂O |
| DL-5-(5'-hydroxyindolylmethyl) hydantoin | D-5-hydroxytryptophan | 0.92 | −15.6° | −16.2° | C = 1 | 4N-HCl |
| DL-5-carboxymethyl hydantion | D-aspartic acid | 0.62 | −26.2° | −26.2° | C = 0.8 | 6N-HCl |
| DL-5-carboxymethyl hydantoin | D-glutamic acid | 0.56 | −30.6° | −32.0° | C = 1 | 2N-HCl |
| DL-5-(4'-imidazoylmethyl hydantoin | D-histidine | 2.05 | −12.2° | −12.4° | C = 0.1 | 6N-HCl |
| DL-5-(4'-aminobutyl) hydantoin | D-lysine | 1.02 | −21.8° | −22.5° | C = 0.8 | " |
| DL-5-(3'-guanidopropyl) hydantoin | D-arginine | 0.69 | −26.2° | −27.2° | " | " |
| DL-5-(3'-aminopropyl) hydantoin | D-ornithine | 0.93 | −24.2° | −25.8° | C = 0.4 | " |
| DL-5-(3'-ureidopropyl) hydantoin | D-citrulline | 1.14 | −24.6° | −25.5° | C = 0.8 | " |
| DL-5-(3'-sulfhydrylethyl) hydantoin | D-homocystein | 3.83 | −76.9° | −79.2° | C = 0.5 | 5N-HCl |
| DL-5-phenyl hydantoin | D-phenylglycine | 3.94 | −151.7° | −155.0° | C = 1 | 1N-HCl |
| DL-5-(p-hydroxyphenyl) hydantoin | D-p-hydroxyphenylglycine | 4.50 | −158.5° | −161.2° | " | " |
| DL-5-(p-chlorophenyl) hydantoin | D-p-chlorophenylglycine | 2.52 | −136.9° | −138.6° | " | " |
| DL-5-(p-methylphenyl) hydantoin | D-p-methylphenylglycine | 1.14 | −147.1° | −149.2° | " | " |
| DL-5-(p-methoxyphenyl) hydantoin | D-p-methoxyphenylglycine | 4.39 | −154.1° | −153.8° | " | " |
| DL-5-(p-benzyloxyphenyl) hydantoin | D-p-benzyloxyphenylglycine | 0.92 | −142.7° | −147.6° | " | " |
| DL-5-(3',4'-dihydroxybenzyl) hydantoin | D-3,4-dihydroxyphenylalanine | 0.87 | +10.9° | +11.7° | " | " |
| DL-5-(3',4'-dimethoxybenzyl) hydantoin | D-3,4-dimethoxyphenylalanine | 0.56 | +10.0° | +10.3° | " | " |
| DL-5-(3',4'-methylenedioxybenzyl) hydantoin | D-3,4-methylenedioxy-phenylalanine | 1.25 | +8.7° | +9.1° | " | " |

EXAMPLE 2

*Achromobacter liquefaciens* AJ 11198 and *Alcaligenes aquamarinus* AJ 11199 were cultured in the same manner as shown in Example 1 in an aqueous culture medium containing, per deciliter, 2 g glucose, 0.5 g (NH₄)₂SO₄, 0.1 g KH₂PO₄, 0.1 g K₂HPO₄, 0.05 g MgSO₄.7H₂O, 1 mg FeSO₄.7H₂O, 1 mg MnSO₄.4H₂O, 1.0 g yeast extract, 0.2 g DL-5-methylmercaptoethyl hydantoin, and 4.0 g CaCO₃ (separately sterilized), at pH 7.0. The cells thus obtained were contacted in 0.1 M phosphate buffer with the 5-substituted-hydantoins shown in Table 2 in the same manner as described in Example 1. The results are shown in Table 2.

Table 2

| 5-substituted-hydantoin used | D-α-amino acid formed | AJ 11198 Amount of D-α-amino acid formed | AJ 11198 Optical rotation | AJ 11199 Amount of D-α-amino acid formed | AJ 11199 Optical rotation | Optical rotation of authentic D-α-amino acid | Measurement condition of optical rotation $[\alpha]_D^{20}$ | |
|---|---|---|---|---|---|---|---|---|
| DL-5-methyl-hydantoin | D-alanine | 0.82mg/dl | −14.4° | 3.08mg/ml | −14.6° | −14.7° | C = 1 | 6N-HCl |
| DL-5-isopropyl hydantoin | D-valine | 0.38 | −27.6° | 3.89 | −26.4° | −27.9° | C = 0.8 | " |
| DL-5-isobutyl hydantoin | D-leucine | 0.32 | −15.3° | 0.76 | −15.0° | −15.2° | C = 0.4 | " |
| DL-5-(1'-methylpropyl) hydantoin | D-isoleucine | 0.68 | −38.9° | 1.42 | −40.1° | −40.77 | " | " |
| DL-5-hydroxymethyl hydantoin | D-serine | 1.92 | −14.5° | 3.86 | −14.3° | −14.6° | C = 1 | 2N-HCl |
| DL-5-(1'-hydroxyethyl) hydantoin | D-threonine | 1.49 | −27.9° | 2.91 | −27.6° | −28.5° | C = 0.6 | H₂O |
| DL-5-sulfhydrylmethyl hydantoin | D-cysteine + D-cystine | 2.21 | +221.6° | 5.20 | +222.1° | +222.5° | C = 0.2 | 1N-HCl |
| DL-5-methylmercaptoethyl hydantoin | D-methionine | 4.04 | −23.8° | 5.96 | −24.8° | −24.1° | C = 0.8 | 6N-HCl |
| DL-5-carbamoylmethyl hydantoin | D-asparagine | 2.67 | −31.0° | 5.02 | −31.3° | −31.3° | C = 0.2 | 3N-HCl |
| DL-5-carbamoylethyl hydantoin | D-glutamine | 3.47 | −6.4° | 4.56 | −6.7° | −6.6° | C = 0.4 | H₂O |
| DL-5-benzyl hydantoin | D-phenylalanine | 2.47 | +33.8° | 3.81 | +33.6° | +34.3° | C = 0.2 | 1N-HCl |
| DL-5-(p-hydroxybenzyl) hydantoin | D-tyrosine | 1.28 | +11.6° | 2.03 | +10.9° | +11.8° | C = 0.5 | 1N-HCl |
| DL-5-indolylmethyl hydantoin | D-tryptophan | 1.41 | +31.8° | 2.64 | +31.6° | +32.5° | C = 0.1 | 1N-HCl |
| DL-5-(5'-hydroxyindolylmethyl) hydantoin | D-5-hydroxytryptophan | 0.49 | −15.4° | 0.82 | −16.1° | −16.2° | C = 1 | 4N-HCl |
| DL-5-carboxymethyl hydantoin | D-aspartic acid | 0.54 | −26.3° | 0.71 | −25.9° | −26.2° | C = 0.8 | 6N-HCl |
| DL-5-carboxyethyl hydantoin | D-glutamic acid | 0.40 | −30.9° | 0.86 | −31.8° | −32.0° | C = 1 | 2N-HCl |
| DL-5-(4'-imidazoylmethyl)hydantoin | D-histidine | 1.09 | −12.2° | 2.52 | −11.9° | −12.4° | C = 0.1 | 6N-HCl |
| DL-5-(4'-aminobutyl) hydantoin | D-lysine | 1.96 | −22.6° | 2.19 | −22.4° | −22.5° | C = 0.8 | " |
| DL-5-(3'-guanidopropyl) hydantoin | D-arginine | 0.24 | −26.4° | 1.03 | −27.0° | −27.2° | " | " |
| DL-5-(3'-aminopropyl) hydantoin | D-ornithine | 0.81 | −24.7° | 1.21 | −25.2° | −25.8° | C = 0.4 | " |
| DL-5-(3'-ureidopropyl) hydantoin | D-citrulline | 0.96 | −25.2° | 1.36 | −25.3° | −25.5° | C = 0.8 | " |
| DL-5-(3'-sulfhydrylethyl) hydantoin | D-homocystein | 2.04 | −77.1° | 4.23 | −78.1° | −79.2° | C = 0.5 | 5N-HCl |
| DL-5-phenyl hydantoin | D-phenylglycine | 4.12 | −152.0° | 4.27 | −153.1° | −155.0° | C = 1 | 1N-HCl |
| DL-5-(p-hydroxyphenyl) hydantoin | D-p-hydroxyphenylglycine | 3.19 | −159.1° | 5.26 | −160.0° | −161.2+ | " | " |
| DL-5-(p-chlorophenyl) hydantoin | D-p-chlorophenylglycine | 2.30 | −137.2° | 2.35 | −138.7° | −138.6° | " | " |
| DL-5-(p-methylphenyl) hydantoin | D-p-methylphenylglycine | 2.09 | −149.1° | 2.26 | −144.9° | −149.2° | " | " |
| DL-5-(p-methoxyphenyl) hydantoin | D-p-methoxyphenylglycine | 4.58 | −151.9° | 4.94 | −154.1° | −153.8° | " | " |
| DL-5-(3',4'-dihydroxybenzyl) hydantoin | D-3,4-dihydroxyphenylalanine | 0.42 | +10.7° | 1.24 | +11.0° | +11.7+ | " | " |
| DL-5-(3',4'-dimethoxybenzyl) hydantoin | D-3,4-dimethoxyphenylalanine | 0.35 | +10.1° | 0.98 | +10.0° | +10.3° | " | " |
| DL-5-(3',4'-methylenedioxybenzyl) hydantoin | D-3,4-methylenedioxyphenylalanine | 0.92 | +8.7° | 1.66 | +9.2° | +9.1° | " | " |
| DL-5-cyanoethyl hydantoin | D-cyanoethylglycine | 4.02 | +27.2° | 5.42 | +26.9° | +28.0° | " | H₂O |

EXAMPLE 3

An aqueous culture medium was prepared such that it contained, per deciliter, 2.0 g glucose, 0.5 g $(NH_4)_2SO_4$, 0.1 g $KH_2PO_4$, 0.1 g $K_2HPO_4$, 0.05 g $MgSO_4.7H_2O$, 1 mg $FeSO_4.7H_2O$, 1 mg $MnSO_4$, 1.0 g yeast extract, 1.0 g peptone, 0.2 g DL-5-methylmercaptoethyl hydantoin and 4.0 g $CaCO_3$ (separately sterilized) and was adjusted to pH 7.0. Fifty ml batches of the aqueous culture medium were placed in 500 ml flasks and were heated to sterilize the same at 120° C. for 15 minutes.

*Moraxella nonliquefaciens* AJ 11221, *Paracoccus denitrificans* AJ 11222, and *Arthrobacter fragilus* AJ 11223 were cultured on bouillon-agar slants at 30° C. for 30 hours. One loopful of inocula of each of the microorganisms was transferred from the bouillon-agar slants into samples of the aqueous culture medium mentioned above. A second cultivation was carried out at 30° C. for 20 hours while the flasks were shaken. The cells in the culture liquids thus obtained were collected by centrifugation, and washed with the same volume of physiological saline as the culture liquid. The 5-substituted-hydantoins listed in Table 3 were converted to D-α-amino acids in the same manner as described in Example 1. The results are shown in Table 3.

Moreover, the amino acids which were formed were isolated and purified, and were ascertained as the D-form by optical rotation measurements.

EXAMPLE 4

*Pseudomonas solanacearum* AJ 11149, *Pseudomonas diminuta* AJ 11151 and *Pseudomonas diminuta* AJ 11152 were used in place of *Pseudomonas caryophylli* AJ 11150 in repetitions of the procedure of Example 1. The results are shown in Table 4.

Table 3

| 5-substituted-hydantoin used | D-α-amino acid formed | Amount of D-α-amino acid formed (mg/ml) | | |
|---|---|---|---|---|
| | | AJ - 11221 | AJ - 11222 | AJ - 11223 |
| DL-5-methyl hydantoin | D-alanine | 3.09 | 0.33 | 2.94 |
| DL-5-isopropyl hydantoin | D-valine | 3.92 | 0.59 | 3.62 |
| DL-5-isobutyl hydantoin | D-leucine | 1.56 | 0.26 | 0.81 |
| DL-5-(1'-methylpropyl) hydantoin | D-isoleucine | 4.29 | 0.24 | 1.03 |
| DL-5-hydroxymethyl hydantoin | D-serine | 3.52 | 2.81 | 3.50 |
| DL-5-(1'-hydroxyethyl) hydantoin | D-threonine | 5.16 | 2.04 | 2.51 |
| DL-5-sulfhydrylmethyl hydantoin | D-cysteine + D-cystine | 5.86 | 3.00 | 4.90 |
| DL-5-methylmercaptoethyl hydantoin | D-methionine | 6.92 | 3.12 | 5.56 |
| DL-5-carbamoylmethyl hydantoin | D-asparagine | 5.19 | 3.82 | 4.94 |
| DL-5-carbamoylethyl hydantoin | D-glutamine | 4.72 | 4.10 | 4.07 |
| DL-5-benzyl hydantoin | D-phenylalanine | 3.41 | 1.26 | 3.61 |
| DL-5-(p-hydroxybenzyl) hydantoin | D-tyrosine | 2.43 | 1.62 | 1.95 |
| DL-5-indolylmethyl hydantoin | D-tryptophan | 2.82 | 1.02 | 2.23 |
| DL-5-(5'-hydroxyindolylmethyl) hydantoin | D-5-hydroxytryptophan | 0.97 | 0.53 | 0.69 |
| DL-5-carboxymethyl hydantoin | D-aspartic acid | 0.72 | 0.49 | 0.68 |
| DL-5-carboxyethyl hydantoin | D-glutamic acid | 1.68 | 0.38 | 0.72 |
| DL-5-(4'-imidazoylmethyl) hydantoin | D-histidine | 2.92 | 1.68 | 2.14 |
| DL-5-(4'-aminobutyl) hydantoin | D-lysine | 1.23 | 0.52 | 1.92 |
| DL-5-(3'-guanidopropyl) hydantoin | D-arginine | 1.21 | 0.62 | 1.07 |
| DL-5-(3'-aminopropyl) hydantoin | D-ornithine | 1.42 | 0.91 | 1.28 |
| DL-5-(3'-ureidopropyl) hydantoin | D-citrulline | 1.42 | 0.78 | 1.38 |
| DL-5-(3'-sulfhydrylethyl) hydantoin | D-homocystein | 5.03 | 3.92 | 4.13 |
| DL-5-phenyl hydantoin | D-phenylglycine | 6.26 | 3.00 | 4.09 |
| DL-5-(p-hydroxyphenyl) hydantoin | D-p-hydroxyphenylglycine | 6.34 | 3.02 | 5.00 |
| DL-5-(p-chlorophenyl) hydantoin | D-p-chlorophenylglycine | 3.14 | 2.96 | 2.39 |
| DL-5-(p-methylphenyl) hydantoin | D-p-methylphenylglycine | 2.97 | 3.01 | 2.30 |
| DL-5-(p-methoxyphenyl) hydantoin | D-p-methoxyphenylglycine | 5.09 | 3.06 | 4.98 |
| DL-5-(p-benzyloxyphenyl) hydantoin | D-p-benzyloxyphenylglycine | 2.09 | 0.92 | 1.09 |
| DL-5-(3',4'-dihydroxybenzyl) hydantoin | D-3,4-dihydrooxyphenylalanine | 1.24 | 0.87 | 1.22 |
| DL-5-(3',4'-dimethoxybenzyl) hydantoin | D-3,4-dimethoxyphenylalanine | 0.98 | 0.42 | 0.96 |
| DL-5-(3',4'-methylenedioxybenzyl) hydantoin | D-3,4-methylenedioxyphenylalanine | 2.06 | 0.95 | 1.73 |
| DL-5-cyanoethyl hydantoin | D-cyanoethylglycine | 6.34 | 3.47 | 5.63 |
| DL-5-(1'-sulfuhydryl-1'-methylethyl) hydantoin | D-penicillamine | 3.92 | 1.46 | 2.92 |

Table 4

| 5-substituted-hydantoin used | D-α-amino acid formed | Amount of D-amino acids formed (mg/ml) | | |
|---|---|---|---|---|
| | | AJ -11149 | AJ -11151 | AJ -11152 |
| DL-5-methyl hydantoin | D-alanine | 1.31 | 2.24 | 0.52 |
| DL-5-isopropyl hydantoin | D-valine | 0.56 | 0.70 | 0.58 |
| DL-5-isobutyl hydantoin | D-leucine | 0.42 | 0.48 | 0.41 |
| DL-5-(1'-methylpropyl) hydantoin | D-isoleucine | 0.87 | 1.12 | 0.34 |
| DL-5-hydroxymethyl hydantoin | D-serine | 3.77 | 3.86 | 2.86 |
| DL-5-(1'-hydroxyethyl) hydantoin | D-threonine | 2.58 | 2.93 | 1.99 |
| DL-5-sulfhydrylmethyl hydantoin | D-cysteine + D-cystine | 4.61 | 5.10 | 3.29 |
| DL-5-methylmercaptoethyl hydantoin | D-methionine | 4.93 | 5.72 | 3.23 |
| DL-5-carbamoylmethyl hydantoin | D-asparagine | 4.02 | 4.47 | 3.84 |
| DL-5-carbamoylethyl hydantoin | D-glutamine | 3.91 | 4.35 | 3.62 |
| DL-5-benzyl hydantoin | D-phenylalanine | 2.58 | 3.81 | 2.22 |
| DL-5-(p-hydroxybenzyl) hydantoin | D-tyrosine | 2.52 | 3.91 | 2.09 |
| DL-5-indolylmethyl hydantoin | D-tryptophan | 1.67 | 2.04 | 1.23 |
| DL-5-(5'-hydroxyindolylmethyl) hydantoin | D-5-hydroxytryptophan | 0.76 | 0.91 | 0.82 |
| DL-5-carboxymethyl hydantoin | D-aspartic acid | 0.46 | 1.38 | 0.48 |
| DL-5-carboxyethyl hydantoin | D-glutamic acid | 0.37 | 1.20 | 0.34 |
| DL-5-(4'-imidazoylmethyl) hydantoin | D-histidine | 1.76 | 2.24 | 1.72 |
| DL-5-(4'-aminobutyl) hydantoin | D-lysine | 0.84 | 1.23 | 0.62 |

Table 4-continued

| 5-substituted-hydantoin used | D-α-amino acid formed | Amount of D-amino acids formed (mg/ml) | | |
|---|---|---|---|---|
| | | AJ -11149 | AJ -11151 | AJ -11152 |
| DL-5-(3'-guanidopropyl) hydantoin | D-arginine | 0.57 | 0.71 | 0.31 |
| DL-5-(3'-aminopropyl) hydantoin | D-ornithine | 0.82 | 1.14 | 0.38 |
| DL-5-(3'-ureidopropyl) hydantoin | D-citrulline | 0.89 | 1.03 | 0.30 |
| DL-5-(3'-sulfhydrylethyl) hydantoin | D-homocystein | 3.54 | 4.90 | 2.45 |
| DL-5-phenyl hydantoin | D-phenylglycine | 4.11 | 5.30 | 3.62 |
| DL-5-(p-hydroxyphenyl) hydantoin | D-p-hydroxyphenylglycine | 3.62 | 4.11 | 2.86 |
| DL-5-(p-chlorophenyl) hydantoin | D-p-chlorophenylglycine | 2.03 | 2.14 | 1.63 |
| DL-5-(p-methylphenyl) hydantoin | D-p-methylphenylglycine | 0.89 | 1.24 | 0.78 |
| DL-5-(p-methoxyphenyl) hydantoin | D-p-methoxyphenylglycine | 3.81 | 3.79 | 3.09 |
| DL-5-(p-benzyloxyphenyl) hydantoin | D-p-benzyloxyphenylglycine | 0.82 | 1.09 | 0.55 |
| DL-5-(3',4'-dihydroxybenzyl) hydantoin | D-3,4-dihydoxyphenylalanine | 1.02 | 0.98 | 0.76 |
| DL-5-(3',4'-dimethoxybenzyl) hydantoin | D-3,4-dimethoxyphenylalanine | 0.62 | 0.51 | 0.49 |
| DL-5-(3',4'-methylenedioxybenzyl) hydantoin | D-3,4-methylenedioxyphenylalanine | 1.18 | 1.32 | 0.59 |

EXAMPLE 5

An aqueous culture medium was prepared in a fashion such that it contained, per deciliter, 2.0 g glucose, 0.5 g $(NH_4)_2SO_4$, 0.1 g $KH_2PO_4$, 0.1 g $K_2HPO_4$, 0.05 g $MgSO_4.7H_2O$, 1 mg $FeSO_4.7H_2O$, 1 mg $MnSO_4.4H_2O$, 1.0 g yeast extract, 1.0 g peptone and 4.0 g $CaCO_3$ (separately sterilized), and was adjusted to a pH of 7.0. Fifty ml batches of the aqueous culture medium were placed in 500 ml flasks which were heated to sterilize at 120° C. for 15 minutes.

*Moraxella nonliquefaciens* AJ 11221, *Paracoccus denitrificans* AJ 11222, and *Arthrobacter fragilus* AJ 11223 were cultured on bouillon-agar slants at 30° C. for 24 hours. One loopful of inocula of each of the microorganisms was transferred from the bouillon-agar slants into samples of the aqueous culture medium mentioned above. Each sample was then cultured at 30° C. with agitation. After cultivation for 24 hours, 0.2 g/dl of a sterilized 5-substituted hydantoin listed in Table 5 was added to each culture broth and cultivation was conducted at 30° C. for an additional 6 hours. The cells in the culture broths thus obtained were harvested by centrifugation, and washed with the same volume of physiological saline as the culture broth.

DL-5-(p-hydroxyphenyl) hydantoin was converted to D-p-hydroxyphenylglycine in the same manner as shown in Example 1. The results are shown in Table 5.

Moreover, the samples of p-hydroxyphenylglycine which formed were isolated and purified. The amino acid samples formed were ascertained as the D-form by measurement of the optical rotation of the samples.

Table 5

| 5-substituted hydantoins added to culture broth | D-p-hydroxyphenylglycine formed (mg/ml) | | |
|---|---|---|---|
| | AJ 11221 | AJ 11222 | AJ 11223 |
| None | 0.96 | 0.42 | 1.28 |
| hydantoin | 0.98 | 0.49 | 1.31 |
| DL-5-methyl hydantoin | 2.41 | 1.03 | 1.68 |
| DL-5-isopropyl hydantoin | 2.39 | 1.09 | 2.03 |
| DL-5-isobutyl hydantoin | 2.21 | 1.02 | 1.96 |
| DL-5-(1'-methylpropyl) hydantoin | 1.96 | 1.41 | 1.73 |
| DL-5-hydroxymethyl hydantoin | 1.98 | 1.37 | 1.97 |
| DL-5-(1'-hydroxyethyl) hydantoin | 2.03 | 1.14 | 2.01 |
| DL-5-methylmercaptoethyl hydantoin | 7.34 | 4.03 | 5.01 |
| DL-5-carbamoylmethyl hydantoin | 2.24 | 1.21 | 1.97 |
| DL-5-carbomoylethyl hydantoin | 2.16 | 1.46 | 2.02 |
| DL-5-benzyl hydantoin | 4.02 | 2.09 | 3.96 |
| DL-5-(p-hydroxybenzyl) hydantoin | 2.23 | 1.04 | 1.91 |
| DL-5-indolymethyl hydantoin | 6.92 | 3.28 | 5.02 |
| DL-5-(5'-hydroxyindolylmethyl) hydantoin | 1.86 | 0.90 | 1.78 |
| DL-5-carboxymethyl hydantoin | 1.92 | 1.34 | 1.86 |
| DL-5-carboxyethyl hydantoin | 1.92 | 1.26 | 1.69 |
| DL-5-(4'-imidazoylmethyl) hydantoin | 1.82 | 0.96 | 1.72 |
| DL-5-(4'-aminobutyl) hydantoin | 2.16 | 1.06 | 1.96 |
| DL-5-(3'-guanidopropyl) hydantoin | 1.92 | 0.96 | 1.94 |
| DL-5-(3'-aminopropyl) hydantoin | 2.01 | 0.92 | 1.98 |
| DL-5-(3'-ureidopropyl) hydantoin | 1.98 | 0.87 | 1.69 |
| DL-5-(3'-sulfhydrylethyl) hydantoin | 2.01 | 1.05 | 2.02 |
| DL-5-phenyl hydantoin | 4.02 | 1.42 | 3.98 |
| DL-5-(p-hydroxyphenyl) hydantoin | 6.12 | 2.23 | 4.64 |
| DL-5-(p-chrolophenyl) hydantoin | 5.28 | 1.58 | 4.18 |
| DL-5-(p-methylphenyl) hydantoin | 4.92 | 1.48 | 3.94 |
| DL-5-(p-methoxyphenyl) hydantoin | 7.96 | 2.42 | 4.89 |
| DL-5-(p-benzyloxyphenyl) hydantoin | 2.95 | 1.04 | 2.39 |
| DL-5-(3',4'-dihydroxybenzyl) hydantoin | 2.83 | 1.01 | 2.65 |
| DL-5-(3',4'-dimethoxybenzyl) hydantoin | 2.41 | 1.21 | 2.24 |
| DL-5-(3',4'-methylenedioxybenzyl) hydantoin | 2.91 | 1.31 | 2.67 |
| DL-5-cyanoethyl hydantoin | 7.23 | 3.29 | 5.20 |

EXAMPLE 6

*Pseudomonas caryophylli* AJ 11150 was cultured in the same manner as described in Example 1, and the resultant culture broth was centrifuged to separate cells. The cells were washed with physiological saline. Twenty-five grams of the cells were suspended in 500 ml of 0.1 M phosphate buffer solution (pH 8.0) which contained 5 g (D-5-(p-hydroxyphenyl) hydantoin or 5 g L-5-(p-hydroxyphenyl) hydantoin. Each reaction mixture was held at 30° C. for 27 hours. Thereafter, each reaction mixture was centrifuged to remove cells and filtered with ultra-filtering membrane. p-Hydroxyphenyl glycine in these filtrates was adsorbed on the H± form of a cation exchange resin ("Diaion" SK-1B) and were eluted with 1 N NH₄OH. Crystals were obtained by cooling after evaporation of the filtrates, and then purified by recrystallization in water-ethanol solution.

Consequently, 3.04 g of crystals were obtained from D-5-(p-hydroxyphenyl) hydantoin and 3.20 g of crystals from L-5-(p-hydroxyphenyl) hydantoin.

These crystals were shown to be the same as authentic D-p-hydroxyphenylglycine by correspondence of the NMR spectra, the Rf values on thin layer chromatograms and paper chromatograms and by optical rotations.

EXAMPLE 7

*Achromobacter liquefaciens* AJ 11198 and *Alcaligenes aquamarinus* AJ 11199 were cultured in the same manner as described in Example 2, and the resultant culture broths were centrifuged to separate cells. The cells were washed with physiological saline.

Twenty-five gram samples of the cells were suspended in 500 ml of 0.1 M phosphate buffer solution (pH 8.0) which contained 5 g D-5-(p-hydroxyphenyl) hydantoin or 5 g L-5-(p-hydroxyphenyl) hydantoin. The reaction mixtures were held at 30° C. for 27 hours. Each mixture was centrifuged to separate the cells and filtered through an ultra-filtration membrane. The p-hydroxyphenylglycine in these filtrates was adsorbed on the H± form of a cation exchange resin ("Diaion" SK-1B) and was eluted with 1 N NH₄OH.

Crystals were obtained from each sample by cooling after evaporating the filtrates. The crystals were purified by recrystallization in water-ethanol solution. By the use of *Achromobacter liquefaciens* AJ 11198, 2.96 g of crystals were obtained from D-5-(p-hydroxyphenyl) hydantoin and 3.12 g of crystals from L-5-(p-hydroxyphenyl) hydantoin. When *Alcaligenes aquamarinus* AJ-11199 was used, 3.02 g of crystals were obtained from D-5-(p-hydroxyphenyl) hydantoin and 3.06 g of crystals were obtained from L-5-(p-hydroxyphenyl) hydantoin.

These crystals were shown to be the same as authentic D-p-hydroxyphenylglycine by correspondence of the NMR spectra, the Rf values of thin layer chromatograms and paper chromatograms and by optical rotations.

EXAMPLE 8

*Moraxella nonliquefaciens* AJ 11221, *Paracoccus denitrificans* AJ 11222 and *Arthrobacter fragilus* AJ 11223 were cultured in the same manner as described in Example 3, and the resultant culture broths were centrifuged to separate the cells. The cells were washed with physiological saline.

Twenty-five grams of the cells were suspended in 500 ml samples of 0.1 M phosphate buffer solution (pH 8.0) each of which contained 5 g of D-5-(p-hydroxyphenyl) hydantoin or 5 g of L-5-(p-hydroxyphenyl) hydantoin. Each reaction mixture was held at 30° C. for 27 hours. Each mixture was then centrifuged to separate the cells and then each solution was filtered with an ultra-filtration membrane. The p-hydroxyphenylglycine in these filtrates was adsorbed on the H± form of a cation exchange resin ("Diaion" SK-1B) and was eluted from the resin with 1 N NH₄OH.

Crystals were obtained from each sample by cooling after evaporating the filtrates. The crystals were purified by recrystallization in water-ethanol solution. In the case of *Moraxella nonliquefaciens* AJ-11221, 4.09 g of crystals were obtained from D-5-(p-hydroxyphenyl) hydantoin and 4.06 g from L-5-(p-hydroxyphenyl) hydantoin. In the case of *Paracoccus deritrificans* AJ 11222, 2.82 g of crystals were obtained from D-5-(p-hydroxyphenyl) hydantoin and 2.86 g of crystals were obtained from L-5-(p-hydroxyphenyl) hydantoin. In the case of *Arthrobacter fragilus* AJ 11223, 3.18 g of crystals were obtained from D-5-(p-hydroxyphenyl) hydantoin and 3.10 g of crystals were obtained from L-5-(p-hydroxyphenyl) hydantoin.

These crystals were shown to be the same as authentic D-p-hydroxyphenyl-glycine by correspondence of the NMR spectra, the Rf values of thin layer chromatograms and paper chromatograms and by optical rotations.

EXAMPLE 9

One loopful inoculum of *Achromobacter liquefaciens* AJ 11198 or *Alcaligenes aquamarinus* AJ 11199 which was previously cultured on a bouillon-agar slant at 30° C. for 24 hours was transferred to 50 ml of a culture medium placed in 500 ml flask. The culture medium contained, per deciliter, 2.0 g glucose, 0.5 g $(NH_4)_2SO_4$, 0.1 g $KH_2PO_4$, 0.1 g $K_2HPO_4$, 0.05 g $MgSO_4.7H_2O$, 1 mg $FeSO_4.7H_2O$, 1 mg $MnSO_4.4H_2O$, 1.0 g yeast extract, 0.2 g DL-5-cyanoethyl hydantoin, and $CaCO_3$ (separately sterilized). The medium was adjusted to pH 7.0, and heated at 120° C. for 15 minutes. Cultivation was conducted at 30° C. for 20 hours, and the cells thus obtained were collected by centrifugation, and washed with an equal volume of physiological saline.

The cells were suspended in 0.1 M phosphate buffer (pH 8.0) to a concentration of 5 g/dl and contained 1 g/dl of 5-substituted hydantoin listed in Table 6 (the final volume of the buffer was 5 ml).

The amino acids formed in the reaction mixture were determined by the methods mentioned before, and ascertained as the D-isomer by measurement of optical rotation. The results are shown in Table 6.

Table 6

| 5-substituted hydantoin used | D-α-amino acid produced | Amount of D-α-amino acid mg/ml | |
|---|---|---|---|
| | | AJ 11198 | AJ 11199 |
| DL-5-phenyl hydantoin | D-phenylglycine | 3.21 | 3.83 |
| DL-5-(p-hydroxyphenyl) hydantoin | D-p-hydroxyphenylglycine | 3.16 | 4.02 |
| DL-5-(p-chlorophenyl) hydantoin | D-p-chlorophenylglycine | 1.82 | 1.96 |
| DL-5-(p-methylphenyl) hydantoin | D-p-methylphenylglycine | 1.64 | 1.88 |
| DL-5-(p-methoxyphenyl) hydantoin | D-p-methoxyphenylglycine | 3.18 | 4.04 |

EXAMPLE 10

A fifty ml portion of a culture medium containing, per deciliter, 1.0 g glucose, 0.5 g (NH$_4$)$_2$SO$_4$, 0.1 g KH$_2$PO$_4$, 0.3 g K$_2$HPO$_4$, 0.05 g MgSO$_4$.7H$_2$O, 1 mg FeSO$_4$.7H$_2$O, 1 mg MnSO$_4$.4H$_2$O, 1.0 g yeast extract and 0.2 g DL-5-methylmercaptoethyl hydantoin was placed in 500 ml flask and heated at 120° C. for 15 minutes. To the medium was added 5 g/dl of CaCO$_3$ which had been previously sterilized. The culture medium was transferred with one loopful inocula of *Pseudomonas caryophylli* AJ 11150, which had been previously grown on a bouillon-agar slant at 30° C. for 24 hours, to the medium which was shaken at 30° C. After 16 hours of cultivation, DL-5-(p-hydroxyphenyl) hydantoin was added to the culture medium in a concentration of 1 g/dl. Cultivation was conducted for an additional 24 hours. In the resultant culture liquid, 5.83 mg/ml of D-p-hydroxyphenylglycine were found.

EXAMPLE 11

A fifty ml portion of a culture medium containing, per deciliter, 2.0 g glucose, 0.5 g (NH$_4$)$_2$SO$_4$, 0.1 g KH$_2$PO$_4$, 0.3 g K$_2$HPO$_4$, 0.05 g MgSO$_4$.7H$_2$O, 1 mg FeSO$_4$.7H$_2$O, 1 mg MnSO$_4$.4H$_2$O, 1.0 g yeast extract, and 0.2 g DL-5-methylmercaptoethyl hydantoin at pH 7.0 was placed in a 500 ml flask and sterilized at 120° C. for 15 minutes. To the medium was added separately sterilized calcium carbonate.

The medium was inoculated with *Achromobacter liquefaciens* AJ 11198 or *Alcaligenes aquamarinus* AJ 11199 which was previously cultured on a bouillon-agar slant at 30° C. for 24 hours, and shaken at 30° C.

After the cultivation had been continued for 16 hours, DL-5-(p-hydroxyphenyl) hydantoin was added to the culture medium in a concentration of 1 g/dl, and further cultivation was performed for 24 hours. Analyses of the resultant culture liquids showed that 0.56 g/dl and 0.58 g/dl of D-p-hydroxyphenylglycine accumulated for AJ 11198 and AJ 11199 respectively.

EXAMPLE 12

The cells of *Pseudomonas caryophylli* AJ 11150 prepared by the method as described in Example 1 were suspended in 0.1 M phosphate buffer in a concentration of 5 g/dl (final volume being 10 ml). The medium was treated with 20 KC supersonic waves for 5 minutes. Then, to 5 ml of the supernatant of the suspension obtained by centrifugation was added DL-5-(p-hydroxyphenyl) hydantoin in a resulting concentration of 1 g/dl. The solution was adjusted to pH 8. The reaction mixture was held at 30° C. for 24 hours, and 7.20 mg/ml D-p-hydroxyphenylglycine were found in the reaction mixture.

EXAMPLE 13

In the method shown in Example 12, the cells of *Achromobacter liquefaciens* AJ 11198 or *Alcaligenes aquamarinus* both prepared by the method shown in Example 2 were used in place of the cells of AJ 11150.

AJ 11198 produced 0.64 g/dl of amino acid product in the reaction mixture, and AJ 11199 produced 0.68 g/dl of the same amino acid product.

EXAMPLE 14

In the method shown in Example 12, the cells of *Moraxella nonliquefaciens* AJ 11221, *Paracoccus denitrificans* AJ 11222 or *Arthrobacter fragilus* AJ 11223 prepared by the method shown in Example 3, were used. In the resultant reaction mixture, AJ 11221, AJ 11222 and AJ 11223 were produced to yield 0.82 g/dl, 0.51 g/dl and 0.67 g/dl of D-p-hydroxyphenylglycine, respectively.

EXAMPLE 15

A one gram amount of the cells of *Pseudomonas caryophylli* AJ 11150 prepared by the method shown in Example 1 was suspended in 4 ml of deionized water and the suspension was cooled. To the suspension was added 750 mg acrylamide and 45 mg methylenebisacrylamide. Nitrogen gas was introduced into the suspension to remove oxygen gas from the suspension, and thereafter 3.5 mg of ammonium persulfate and 8 µl of N,N'dimethylaminopropionitrile was added to the suspension and cooled for 1 hour. The gel thus formed was passed through a 50 mesh wire gauze, and 2 g of the gel was put into 5 ml of 0.1 M phosphate buffer (pH 8.0) containing 1 g/dl of DL-5-(p-hydroxyphenyl) hydantoin. The reaction mixture was then held at 30° C. for 24 hours, and 3.24 mg/ml of D-p-hydroxyphenylglycine was found in the reaction mixture.

By a procedure analogous to that mentioned above, *Achromobacter liquefaciens* AJ 11198, *Alcaligenes aquamarinus* AJ 11199, *Moraxella nonliquefaciens* AJ 11221, *Paracoccus denitrificans* AJ 11222 and *Arthrobacter fragilus* AJ 11223 led to the production of 0.34 g/dl, 0.35 g/dl, 0.50 g/dl, 0.28 g/dl, and 0.38 g/dl D-p-hydroxyphenylglycine, respectively in the reaction mixture.

EXAMPLE 16

An aqueous culture medium containing, per deciliter, 2.0 g glucose, 0.5 g (NH$_4$)$_2$SO$_4$, 0.1 g KH$_2$PO$_4$, 0.1 g K$_2$HPO$_4$, 0.05 g MgSO$_4$.7H$_2$O, 1 mg FeSO$_4$.7H$_2$O, 1 mg MnSO$_4$.4H$_2$O, 1.0 g yeast extract and 4.0 g CaCO$_3$ was adjusted to pH 7.0, and 50 ml batches of the culture medium were placed in 500 ml flasks which were heated at 120° C. for 15 minutes.

*Pseudomonas caryophylli* AJ 11150 previously cultured on a bouillon-agar slant at 30° C. for 24 hours was inoculated into the culture medium mentioned above, and cultured at 30° C. After 16 hours of cultivation the 5-substituted hydantoins shown in Table 7 which had been previously heated to sterilize the same were placed in samples of the culture medium at a concentration of 0.2 g/dl, and additional cultivation was performed for 6 hours. Cells in the culture liquids thus obtained were collected by centrifugation, and washed with the physiological saline.

Five ml samples of 0.1 M phosphate buffer (pH 8.0) containing 1 g/dl DL-p-hydroxyphenyl hydantoin and 5 g/dl of the cells mentioned above were held at 30° C. for 16 hours. The amounts of D-p-hydroxyphenylglycine produced in each reaction mixture are shown in Table 7.

Table 7

| 5-subsituted hydantoin added to the culture medium | D-p-OH-phenylglycine produced (mg/ml) |
| --- | --- |
| none | 0.92 |
| hydantoin | 0.98 |
| DL-5-methyl hydantoin | 1.72 |
| DL-5-isopropyl hydantoin | 2.35 |
| DL-5-isobutyl hydantoin | 2.04 |
| DL-5-(1'-methylpropyl) hydantoin | 1.82 |
| DL-5-hydroxymethyl hydantoin | 1.96 |
| DL-5-(1'-hydroxyethyl) hydantoin | 2.31 |

Table 7-continued

| 5-subsituted hydantoin added to the culture medium | D-p-OH-phenylglycine produced (mg/ml) |
|---|---|
| DL-5-methylmercaptoethyl hydantoin | 5.21 |
| DL-5-carbamoylmethyl hydantoin | 1.99 |
| DL-5-carbamoylethyl hydantoin | 2.16 |
| DL-5-benzyl hydantoin | 3.99 |
| DL-5-(p-hydroxybenzyl) hydantoin | 2.04 |
| DL-5-indolylmethyl hydantoin | 5.06 |
| DL-5-(5'-hydroxyindorylmethyl hydantoin | 2.03 |
| DL-5-carboxymethyl hydantoin | 1.92 |
| DL-5-carboxyethyl hydantoin | 1.78 |
| DL-5-(4'-imidazolymethyl) hydantoin | 1.72 |
| DL-5-(4'-aminobutyl) hydantoin | 1.99 |
| DL-5-(3'-guanidpropyl) hydantoin | 2.03 |
| DL-5-(3'-aminopropyl) hydantoin | 1.92 |
| DL-5-(3'-ureidpropyl) hydantoin | 1.70 |
| DL-5-(3'-sulfhydrylethyl) hydantoin | 2.06 |
| DL-5-phenyl hydantoin | 3.99 |
| DL-5-(p-hydroxyphenyl) hydantoin | 4.72 |
| DL-5-(p-chlorophenyl) hydantoin | 4.19 |
| DL-5-(p-methylphenyl) hydantoin | 4.00 |
| DL-5-(p-methoxyphenyl) hydantoin | 4.92 |
| DL-5-(p-benzyloxyphenyl) hydantoin | 2.42 |
| DL-5-(3',4'-dihydroxybenzyl) hydantoin | 2.88 |
| DL-5-(3',4'-dimethoxybenzyl) hydantoin | 2.46 |
| DL-5-(3',4'-methylenedioxy) hydantoin | 2.72 |
| DL-5-cyanoethyl hydantoin | 5.42 |

EXAMPLE 17

Two 300 ml batches of a culture medium containing, per deciliter, 2 g glucose, 0.5 g $(NH_4)_2SO_4$, 0.1 g $KH_2PO_4$, 0.02 g $CaCl_2.2H_2O$, 0.3 g $K_2HPO_4$, 0.05 g $MgSO_4.7H_2O$, 1 mg $FeSO_4.7H_2O$, 1 mg $MnSO_4.4H_2O$, and 1.0 g yeast extract at pH 7.0 were placed in 1 liter fermentation vessels. The vessels were heated at 120° C. for 15 minutes to sterilize the same.

Six ml samples of seed cultures of *Moraxella nonliquefaciens* AJ 11221 and *Pseudomonas caryophylli* AJ 11150 which had been previously cultured at 30° C. for 24 hours in the same medium mentioned above were transferred into fermentation vessels. Cultivation was conducted under aerobic conditions at 30° C. at an adjusted pH of 7.0 with gaseous ammonia. After 16 hours and 22 hours of cultivation, DL-5-(p-hydroxyphenyl) hydantoin samples were added to each culture medium to achieve a concentration of 0.2 g/dl.

After 25 hours from initiation of cultivation, nitrogen gas was introduced into the fermentation vessels, and the temperature was raised to 40° C. Then, crystals of DL-5-(p-hydroxyphenyl) hydantoin were added to each culture medium to a concentration of 3 g/dl. Each culture medium was held for 40 hours at 40° C. while nitrogen was continually introduced into each flask. The pH was adjusted to 7.0 with 1 N HCl. AJ 11221 produced 2.75 g/dl of D-p-hydroxyphenylglycine and AJ 11150 produced 2.69 g/dl of the same.

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A method for producing a D-α-amino acid, which comprises:

contacting a 5-substituted hydantoin with an effective amount of an enzyme capable of converting the 5-substituted hydantoin directly to the D-α-amino acid, produced by a microorganism belonging to the genus Pseudomonas, Achromobacter, Alcaligenes, Moraxella, Paracoccus or Anthrobacter, in an aqueous medium at a pH in the range from 4 to 9, said microorganism being capable of utilizing the D-isomer of said 5-substituted hydantoin as the sole nitrogen source, but substantially incapable of utilizing the L-isomer of said 5-substituted hydantoin as the nitrogen source and the substituent of said 5-position being such that upon reaction with said enzyme, an optically active D-α-amino acid isomer is produced; and recovering the D-α-amino acid which accumulates in the aqueous medium.

2. The method of claim 1, wherein the microorganism is

*Pseudomonas solanacearum* AJ 11149 (NRRL B-11,255),
*Pseudomonas caryophilli* AJ 11150 (NRRL B-11,256),
*Pseudomonas diminuta* AJ 11151 (NRRL B-11,257),
*Pseudomonas diminuta* AJ 11152 (NRRL B-11,258),
*Achromobacter liquefaciens* AJ 11198 (NRRL B-11,259),
*Alcaligenes aquamarinus* AJ 11199 (NRRL B-11,260),
*Moraxella nonliquefaciens* AJ 11221 (NRRL B-11,261),
*Paracoccus denitrificans* AJ 11222 (NRRL B-11,262), or
*Arthrobacter fragilus* AJ 11223 (NRRL B-11,263).

3. The method of claim 1, wherein the enzyme is produced by culturing the microorganism in an aqueous culture medium containing at least one 5-substituted hydantoin.

4. The method of claim 1, wherein the 5-substituted-hydantoin is a 5-alkyl hydantoin.

5. The method of claim 1, wherein the 5-substituted-hydantoin is a 5-(substituted alkyl) hydantoin.

6. The method of claim 1, wherein the 5-substituted-hydantoin is a 5-aryl-hydantoin.

7. The method of claim 1, wherein the 5-substituted-hydantoin is a 5-(substituted-aryl)-hydantoin.

8. The method of claim 1, wherein the 5-substituted-hydantoin is a 5-aralkyl hydantoin.

9. The method of claim 1, wherein the 5-substituted-hydantoin is a 5-(substituted aralkyl) hydantoin.

10. The method of claim 1, wherein the 5-substituted-hydantoin is 5-phenyl hydantoin or 5-p-hydroxyphenyl hydantoin.

11. The method of claim 1, wherein the 5-substituted-hydantoin is contacted with the enzyme in the aqueous culture medium in which the microorganism is cultured.

12. The method of claim 1, wherein the 5-substituted-hydantoin is contacted with the enzyme in an aqueous reaction medium containing as the enzyme source the cells of the microorganism, the homogenate of the cells, cells which has been treated with supersonic waves, freeze-dried cells, cells dried by treatment with an organic solvent, protein fractions separated from cells which have the enzyme activity, or immobilized cells.

13. The method of claim 1, wherein said 5-substituent of said hydantoin is a straight, branched or cyclic saturated aliphatic hydrocarbon radical; a straight, branched or cyclic unsaturated aliphatic hydrocarbon radical; a straight, branched or cyclic saturated or unsaturated aliphatic hydrocarbon radical of which at least one hydrogen atom is substituted with at least one substituent; an aromatic hydrocarbon radical; an aromatic hydrocarbon radical of which at least one hydrogen atom is substituted with at least one substituent; a heterocyclic radical or heterocyclic residues of which at least one hydrogen atom is substituted with at least one substituent.

* * * * *